(12) United States Patent
Rader et al.

(10) Patent No.: US 9,273,136 B2
(45) Date of Patent: Mar. 1, 2016

(54) FULLY HUMAN ANTI-HUMAN NKG2D MONOCLONAL ANTIBODIES

(75) Inventors: Christoph Rader, Olney, MD (US); Ka Yin Kwong, Gaithersburg, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1336 days.

(21) Appl. No.: 13/057,092

(22) PCT Filed: Jul. 31, 2009

(86) PCT No.: PCT/US2009/052387
§ 371 (c)(1),
(2), (4) Date: Mar. 14, 2011

(87) PCT Pub. No.: WO2010/017103
PCT Pub. Date: Feb. 11, 2010

(65) Prior Publication Data
US 2011/0150870 A1    Jun. 23, 2011

Related U.S. Application Data

(60) Provisional application No. 61/086,027, filed on Aug. 4, 2008.

(51) Int. Cl.
*C07K 16/00* (2006.01)
*C07K 16/28* (2006.01)
*A61K 39/00* (2006.01)

(52) U.S. Cl.
CPC ....... *C07K 16/2851* (2013.01); *A61K 2039/505* (2013.01); *C07K 2317/21* (2013.01); *C07K 2317/55* (2013.01); *C07K 2317/56* (2013.01); *C07K 2317/565* (2013.01); *C07K 2317/73* (2013.01); *C07K 2317/76* (2013.01); *C07K 2317/92* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 3,832,253 A | 8/1974 | Palma et al. | |
| 3,854,480 A | 12/1974 | Zaffaroni | |
| 4,452,775 A | 6/1984 | Kent | |
| 4,667,014 A | 5/1987 | Nestor, Jr. et al. | |
| 4,748,034 A | 5/1988 | de Rham | |
| 5,075,109 A | 12/1991 | Tice et al. | |
| 5,239,660 A | 8/1993 | Ooi | |
| 2005/0158307 A1 | 7/2005 | Spies et al. | |
| 2006/0280755 A1 | 12/2006 | Baron et al. | |
| 2007/0077241 A1 | 4/2007 | Spies et al. | |

FOREIGN PATENT DOCUMENTS

WO    WO 2009/077483 A1    6/2009

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Alter et al., *J. Immunol Methods*, 294, 15-22 (2004).
Baskar et al., *Clin. Cancer Res.*, 14 (2), 396-404 (2008).
Bauer et al., *Science*, 285, 727-729 (1999).
Betts et al., *Methods Cell Biol.*, 75 (Ch. 20), 497-512 (2004).
Billadeau et al., *Nat. Immunol.*, 4 (6), 557-564 (2003).
Corvaisier et al., *J. Immunol.*, 175 (8), 5481-5488 (2005).
De Haard et al., *J. Biol. Chem.*, 274 (26), 18218-18230 (1999).
Ehrlich et al., *J. Immunol.*, 174, 1922-1931 (2005).
Griffiths et al., *EMBO J.*, 13 (14), 3245-3260 (1994).
Hofer et al., *J. Immunol. Methods*, 318, 75-87 (2007).
Hoogenboom, *Nat. Biotechnol.*, 23 (9), 1105-1116 (2005).
Internet Document "Monoclonal Anti-human NKG2D Antibody," http://www.rndsystems.com/pdf/mab139.pdf (2006).
Karimi et al., *J. Immunol.*, 175, 7819-7828 (2005).
Kwong et al., *Curr Protoc Protein Sci, Supp.* 55, 6.10.1-6.10.14 (2009).
Kwong et al., *J. Mol. Bio.*, 384, 1143-1156 (2008).
Lee et al., *J. Mol. Biol.*, 340, 1073-1093 (2004).
Li et al., *Immunity*, 16, 77-86 (2002).
Li et al., *Nat. Immunol.*, 2 (5), 443-451 (2001).
Ogasawara et al., *Immunity*, 20, 757-767 (2004).
Ogasawara et al., *Nature Immunol.*, 6 (9), 938-945 (2005).
Pende et al., *Euro. J. Immunol.*, 31 (4), 1076-1086 (2001).
Pogge Von Strandmann et al., *Blood*, 107 (5), 1955-1962 (2006).
Popkov et al., *J. Mol. Biol.*, 325, 325-335 (2003).
Rader et al., *FASEB J.*, 16, 2000-2002 (2002).
Rader, *Drug Discov. Today*, 6 (1), 36-43 (2001).
Rader, *Methods Mol. Biol.*, 525, 101-128 (2009).
Rincon-Orozco et al., *J. Immunol.*, 175 (4), 2144-2151 (2005).
Rothe et al., *J. Mol. Biol.*, 376, 1182-200 (2008).
Steigervvald et al., *mAbs*, 1 (2), 115-127 (2009).
Verneris et al., *Blood*, 103 (8), 3065-3072 (2004).
Vilarinho et al., *PNAS*, 104 (46), 18187-18192 (2007).
Wolan et al., *Nat. Immunol.*, 2 (3), 248-254 (2001).
Wu et al., *Nat. Biotechnol.*, 23 (9), 1137-1146 (2005).
Zhang et al., *J. Immunol.*, 179, 4910-4918 (2007).

* cited by examiner

*Primary Examiner* — Brad Duffy
(74) *Attorney, Agent, or Firm* — Leydig, Voit & Mayer, Ltd.

(57) ABSTRACT

The invention relates to isolated fully human monoclonal antibodies having specificity for human NKG2D and compositions thereof. The invention further relates to methods for using such antibodies in treating diseases or conditions such as cancer, autoimmune disease, or infectious disease.

16 Claims, 9 Drawing Sheets

Figure 1:
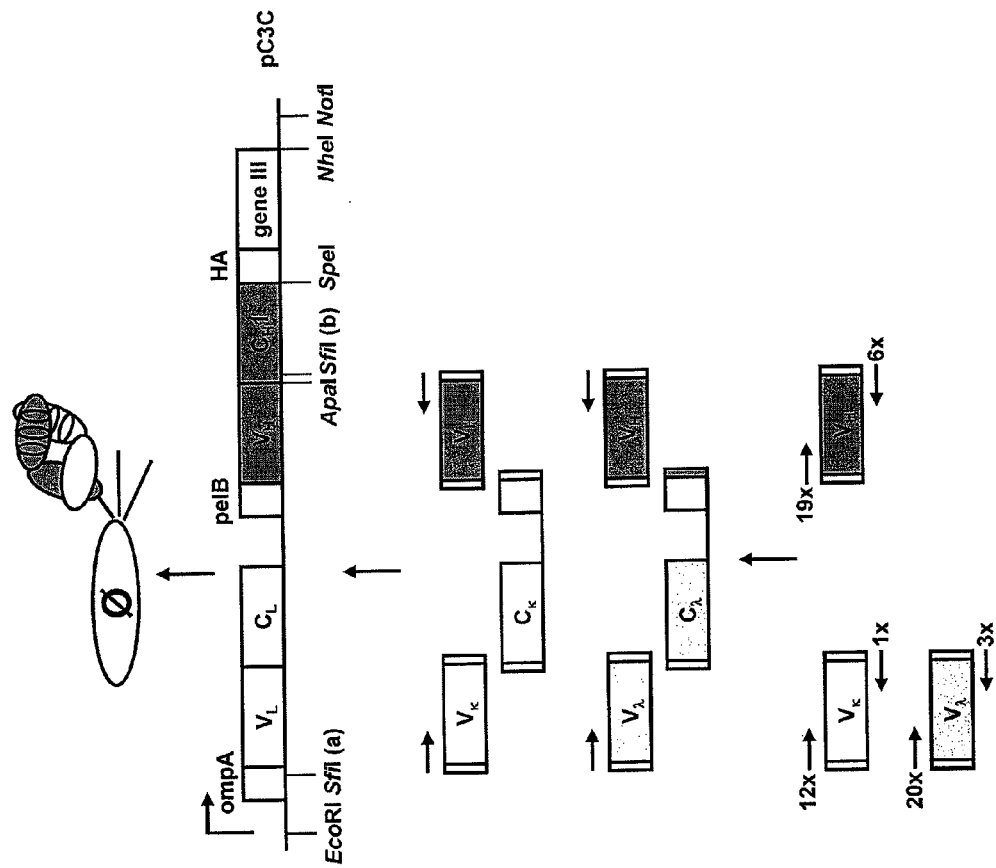

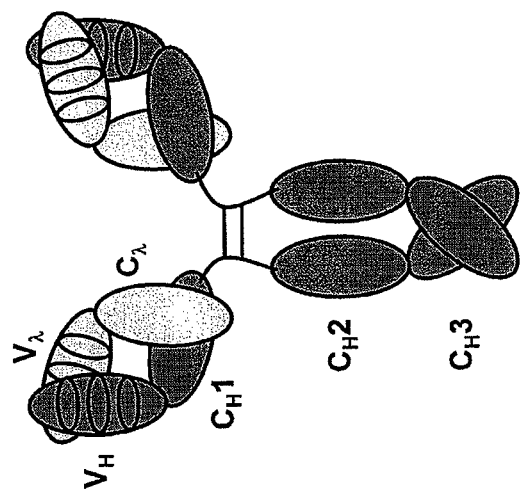
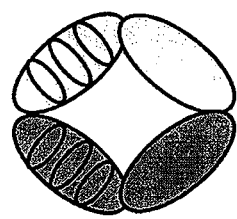
Fig. 2B

Fig. 3

Vλ

```
         FR1                              CDR1              FR2            CDR2    FR3
Vλ 3-21  SY-------P------K-----T-         --NN-GS-----      -------------V- ---S--- -------S-------T-------
KYK-1.0  QPVLTQPSSVSVAPGETARIPC           GGDDIETKSVH       WYQQKPGQAPVLVIY DDDDRPS GIPERFFGSNSGNTATLSISRVEAGDEADYYC
         **  *  **  ******* *             * ***********     * * *           * **    ***  *   * **  ****  *****
KYK-2.0  QSALTQPASVSGSPGQSITISC           SGSSSNIGNNAVN     WYQQLPGKAPKLLIY YDDLLPS GVSDRFSGSKSGTSAFLAISGLQSEDEADYYC
Vλ 1-36  --V----P---EA-R-RV----                                                      -----------S--------------------
```

```
         CDR3              FR4
KYK-1.0  QVWDDNNDEWV       FGGGTQLTVL
         **  *****         *
KYK-2.0  AAWDDSLNGPV       FGGGTKLTVL
```

VH

```
         FR1                              CDR1    FR2              CDR2              FR3
VH 3-30  Q--------                        -----   ------------     ----------------  ------------------------------
KYK-1.0  EVQLVESGGGVVQPGGSLRLSCAASGFTFS    SYGMH   WVRQAPGKGLEWVA   FIRYDGSNKYYADSVKG RFTISRDNSKNTLYLQMNSLRAEDTAVYYCAK
           *
KYK-2.0  QVQLVESGGGLVKPGGSLRLSCAASGFTFS    SYGMH   WVRQAPGKGLEWVA   FIRYDGSNKYYADSVKG RFTISRDNSKNTLYLQMNSLRAEDTAVYYCAK
VH 3-30  --------V--Q---
```

```
         CDR3              FR4
KYK-1.0  DR...FGYYLDY      WGQGTLVTVSS
         ****  *   *
KYK-2.0  DRGLGDGTYFDY      WGQGTTVTVSS
```

US 9,273,136 B2

FULLY HUMAN ANTI-HUMAN NKG2D MONOCLONAL ANTIBODIES

CROSS-REFERENCE TO RELATED APPLICATIONS

This patent application is a U.S. National Phase of International Patent Application No. PCT/US09/52387, filed Jul. 31, 2009, which claims the benefit of U.S. Provisional Patent Application No. 61/086,027, filed Aug. 4, 2008, which are each incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 9,431 Byte ASCII (Text) file named "707572ST25.TXT," created on Jan. 25, 2011.

BACKGROUND OF THE INVENTION

Antibody therapies have been developed for use in treating a wide range of conditions including autoimmune diseases or disorders, infectious diseases, and cancers. Such therapies are useful but can be associated with undesirable immunogenicity, and may be damaging to healthy cells and tissues.

Additional therapies for autoimmune diseases or conditions, infectious diseases, and cancers are desirable. Such therapies desirably would have broad and potent therapeutic activity while minimizing immunogenicity and damage to non-diseased cells.

BRIEF SUMMARY OF THE INVENTION

The invention provides a fully human monoclonal antibody to NKG2D, which is an activating receptor found on natural killer (NK) cells and a costimulatory receptor on certain T cells.

In particular, the invention provides an isolated antibody having specificity for human NKG2D, comprising (a) a heavy chain having at least 90% identity to a sequence selected from the group consisting of SEQ ID NO:1 and SEQ ID NO:9; (b) a light chain having at least 90% identity to a sequence selected from the group consisting of SEQ ID NO:2 and SEQ ID NO:10; or (c) both a heavy chain of (a) and a light chain of (b).

In another aspect, the invention provides an isolated antibody having specificity for human NKG2D, comprising at least one CDR having a sequence selected from the group consisting of SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, and SEQ ID NO:16.

The invention further provides for therapeutic compositions comprising an antibody as described above and a pharmaceutically acceptable excipient.

In yet another aspect, the invention provides methods of treating a disease or condition in a subject comprising administering a therapeutically effective amount of such an antibody or a composition thereof.

BRIEF DESCRIPTION OF THE DRAWING(S)

FIG. 1 is a schematic that depicts the generation of a naïve human Fab library in phage display vector pC3C.

Figure 2A:
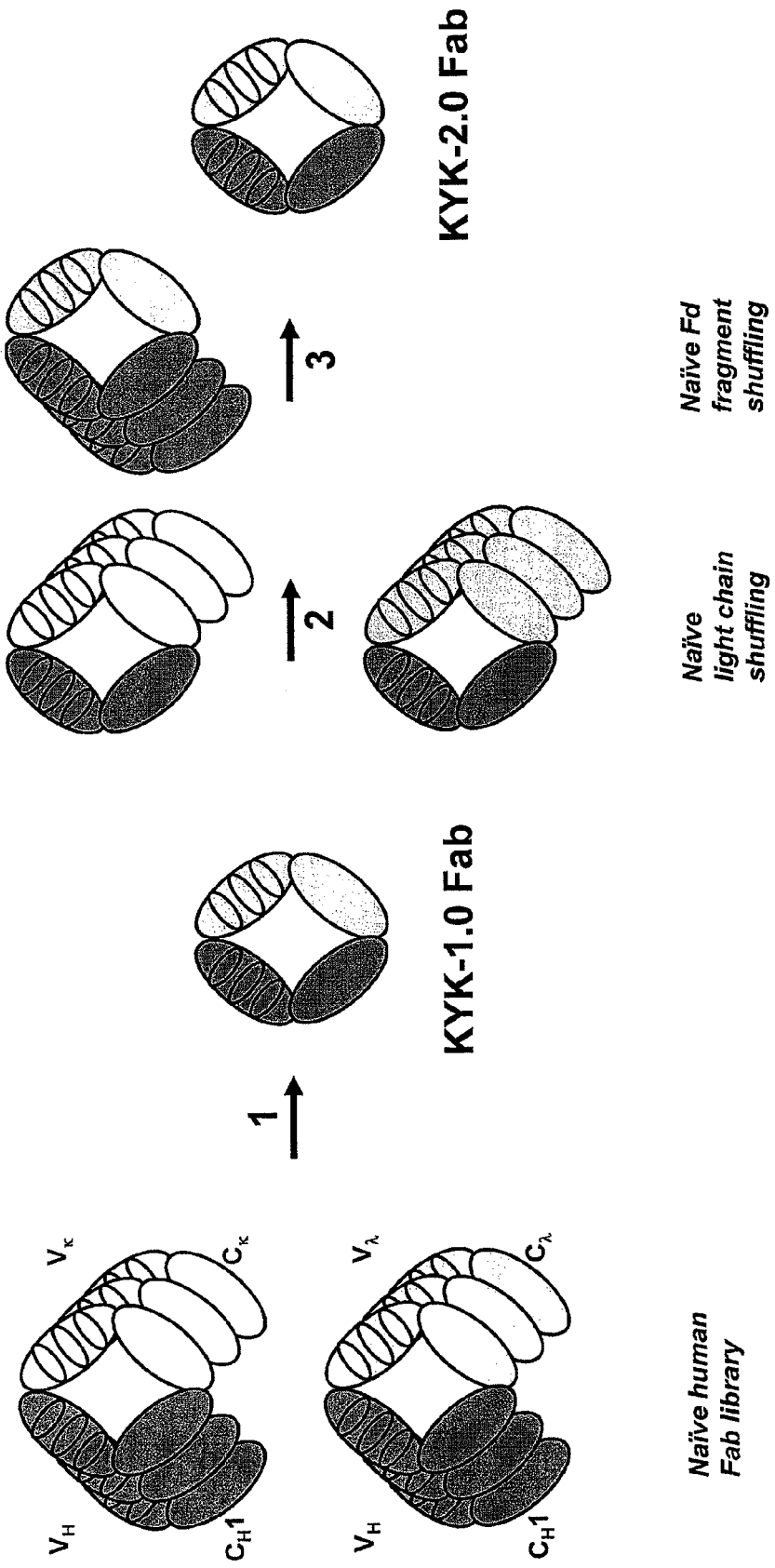

FIG. 2A is a schematic that depicts the selection and affinity maturation of a human anti-human NKG2D mAb. Step 1 depicts selection of a human Fab, termed KYK-1.0 Fab, with high specificity for human NKG2D from a naïve human Fab library consisting of 1.5 billion independent human Fab with both kappa and lambda light chains. Step 2 depicts the first chain shuffling step, in which the human lambda light chain of KYK-1.0 Fab was replaced with a naïve human lambda and kappa light chain library which was then re-selected by phage display against human NKG2D. Step 3 depicts the second chain shuffling step, in which the human heavy chain fragment, also termed Fd fragment, of KYK-1.0 Fab was replaced with a naïve human Fd fragment library which was then also re-selected against human NKG2D.

FIG. 2B is a schematic that depicts the conversion of KYK-2.0 Fab to IgG1 using mammalian expression vector PIGG expressed in human embryonic kidney (HEK) 293F cells.

FIG. 3 is an amino acid sequence alignment of the variable domains $V_\lambda$ and $V_H$ of KYK-1.0 and KYK-2.0 with their corresponding human germlines (only V genes). Shown are the 4 framework regions (FR) and 3 complementarity determining regions (CDR). Dashes indicate amino acids that are identical in the human germlines. Differences between KYK-1.0 and KYK-2.0 are highlighted by asterisks.

Figure 4:
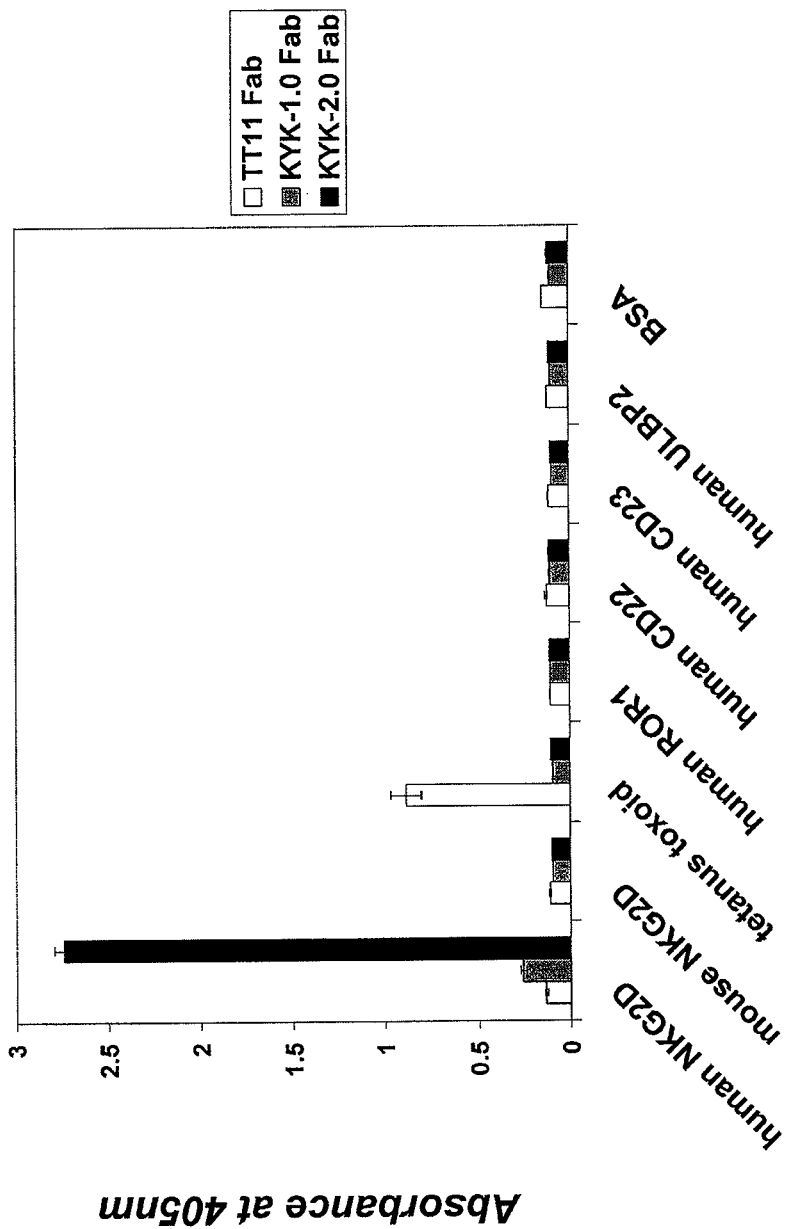

FIG. 4 is a graph that depicts the absorbance analysis of KYK-1.0 and KYK-2.0 Fab specificity using ELISA. Shown is the binding of KYK-1.0 and KYK-2.0 Fab to a panel of proteins immobilized on an ELISA 96-well plate at 100 ng/well. TT11 Fab, which was selected from the same naïve human Fab library against tetanus toxoid, served as control. Error bars indicate mean±SEM (n=3).

Figure 5:
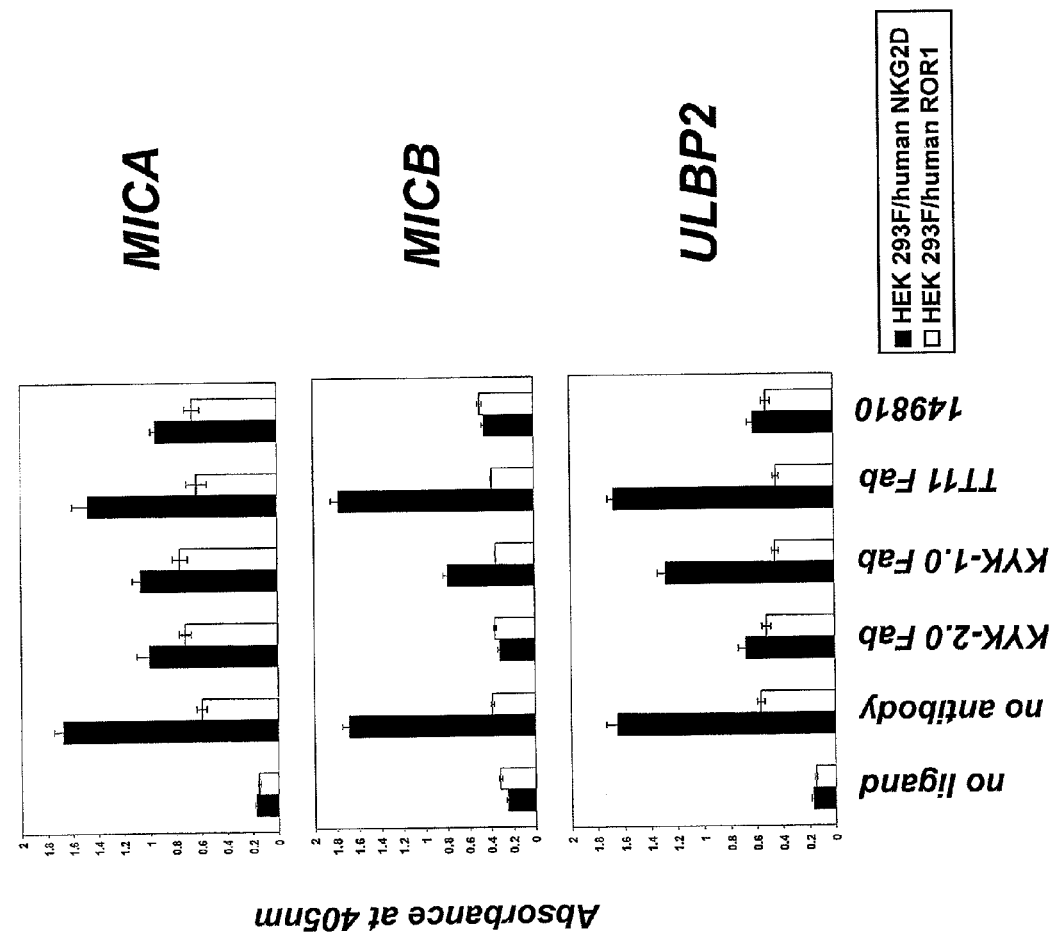

FIG. 5 is a graph that depicts the absorbance analysis of KYK-1.0 and KYK-2.0 Fab for interfering with NKG2D receptor/ligand interactions. In an ELISA 96-well plate, HEK 293F transfectants that stably express cell surface human NKG2D (black bars) or human ROR1 (white bars) were incubated with recombinant human MICA-Fc, MICB-Fc, or ULBP2-Fc in the presence or absence of KYK-1.0 Fab, KYK-2.0 Fab, TT11 Fab (negative control), and mouse anti-human NKG2D mAb 149810 (positive control). Biotinylated goat anti-human Fc polyclonal antibodies followed by streptavidin conjugated to horseradish peroxidase were used for detecting ligand binding. Error bars indicate mean±SEM (n=4).

Figure 6:
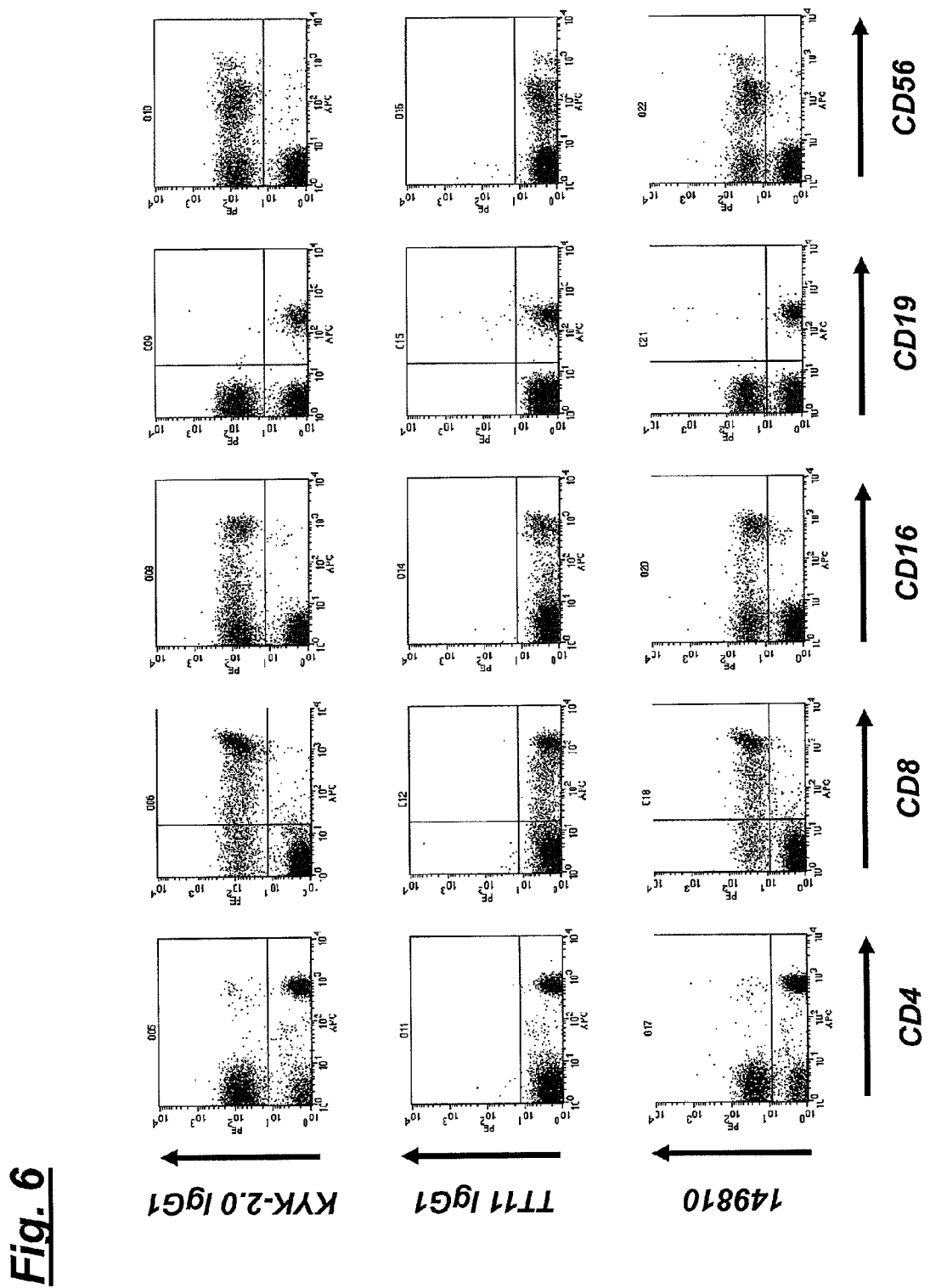

FIG. 6 is a series of flow cytometry analysis plots of the binding of KYK-2.0 IgG1 to human PBMC subpopulations. Freshly isolated human PBMC were stained with APC-coupled mouse mAb to CD4, CD8, CD16, CD19, or CD56 (x axes) and with biotinylated KYK-2.0 IgG1 or TT11-IgG1 (negative control) followed by streptavidin-PE (y axes). PE-coupled mouse anti-human NKG2D mAb 149810 was used as positive control.

Figure 7:
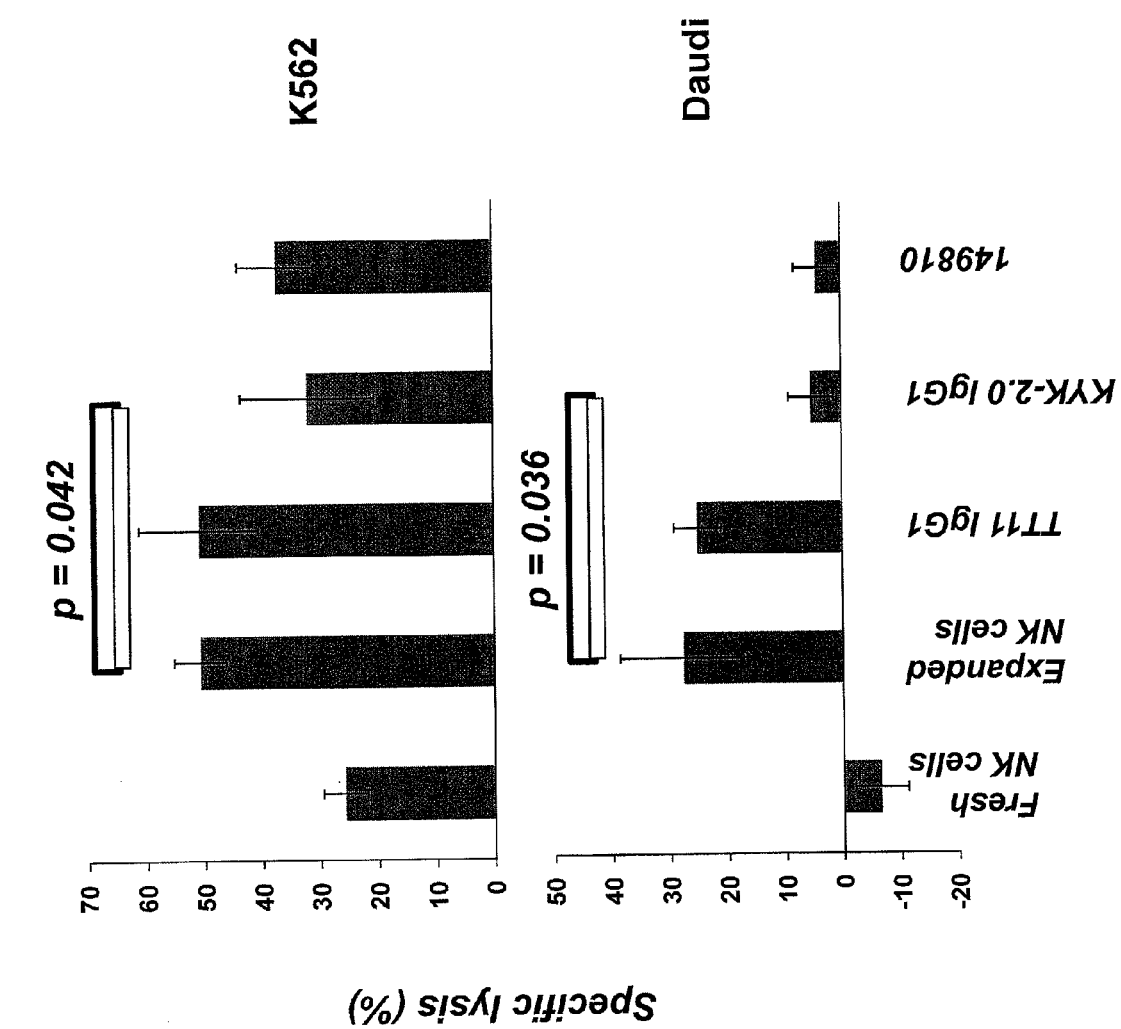

FIG. 7 is a graph that depicts cytolytic activity of ex vivo expanded human NK cells by KYK-2.0 IgG1 measured as specific lysis based on $^{51}$Cr release. Human K562 (top) or Daudi cells (bottom) were labeled with $^{51}$Cr and incubated with fresh human NK cells or ex vivo expanded human NK cells at an E:T ratio of 40:1 in the absence or presence of KYK-2.0 IgG1, TT11 IgG1 (negative control), and mouse anti-human NKG2D mAb 149810 (positive control). Error bars indicate mean±SD (n=3); the probability (p) is based on a paired one-tailed t-test.

Figure 8:
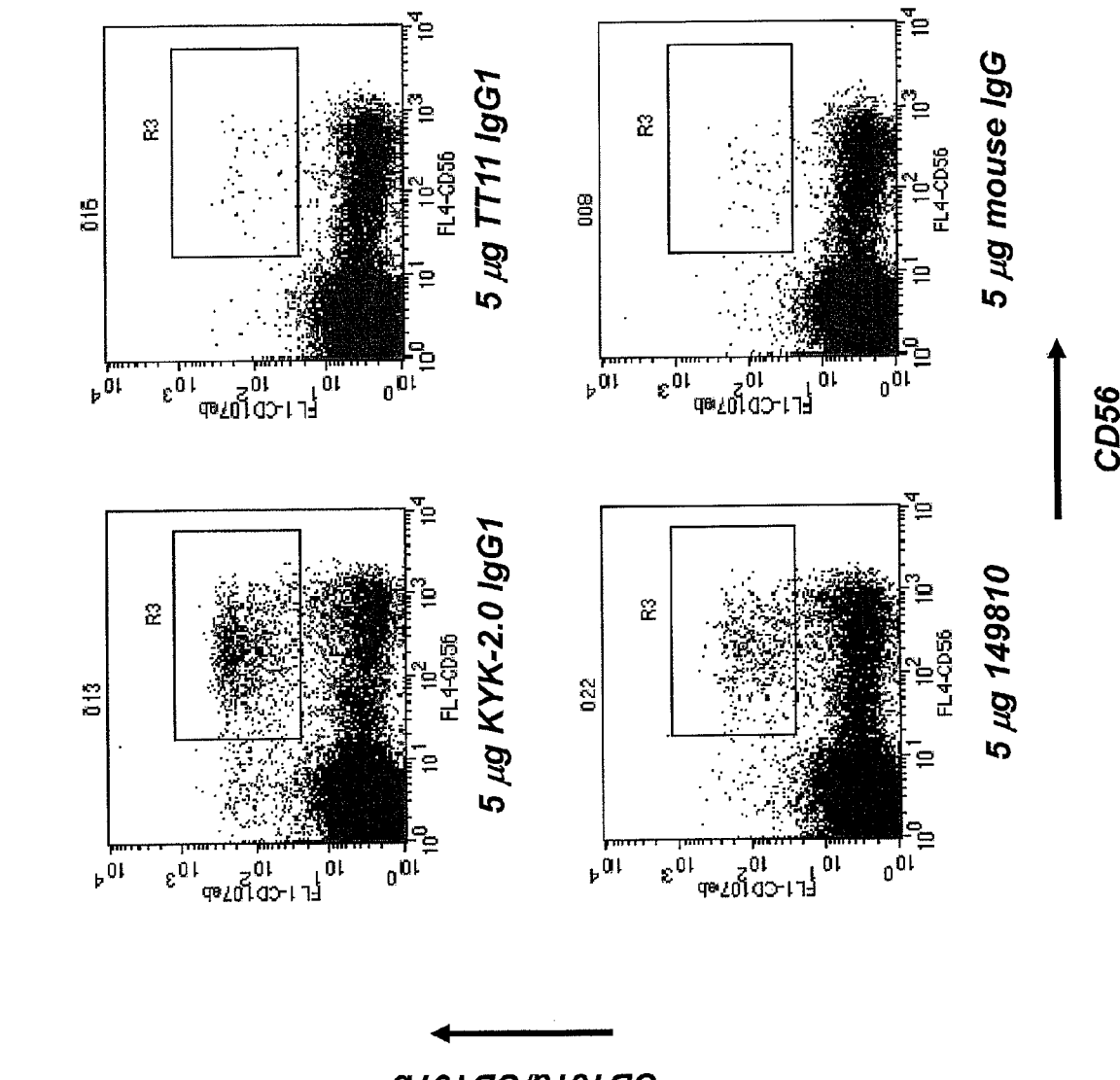

FIG. 8 is a series of flow cytometry analysis plots of the degranulation of human NK cells by immobilized KYK-2.0 IgG1. Freshly isolated human PBMC were stimulated with IL-2 and then incubated with immobilized mAbs. Activation was detected with a mixture of FITC-coupled mouse anti-human CD107a and mouse anti-human CD107b mAbs. NK cells were detected with an APC-coupled mouse anti-human CD56 mAb. CD56+ CD107a/CD107b+ cells are gated (R3). Typical results for one healthy donor are shown. The percentage of degranulated NK cells (CD56+ CD107a/CD107b+) among total NK cells (CD56+) is shown in Table 2 of Example 4 herein for four different healthy donors.

DETAILED DESCRIPTION OF THE INVENTION

The invention provides an antibody, particularly a fully human monoclonal antibody, to human NKG2D, as well as related methods and compositions thereof.

The antibody is an isolated antibody having specificity for human NKG2D, comprising (a) a heavy chain having at least 90% identity to a sequence selected from the group consisting of SEQ ID NO:1 (KYK1.0 heavy chain sequence) and SEQ ID NO:9 (KYK2.0 heavy chain sequence); (b) a light chain having at least 90% identity to a sequence selected from the group consisting of SEQ ID NO:2 (KYK1.0 light chain sequence) and SEQ ID NO:10 (KYK2.0 light chain sequence); or (c) both a heavy chain of (a) and a light chain of (b). In a preferred embodiment, the antibody comprises both a heavy chain of (a) and a light chain of (b).

The antibody can be an isolated antibody having specificity for human NKG2D, comprising a heavy chain having at least 90% identity to a sequence such as SEQ ID NO:1 (KYK1.0 heavy chain sequence) or SEQ ID NO:9 (KYK2.0 heavy chain sequence). In other embodiments, the percentage identity can be at least 91%, 92%, 93%, 94%, 95%, 96%, 97%, 98%, or 99%, or even 100%. In preferred embodiments, the heavy chain has at least 95% identity to SEQ ID NO:1 (KYK1.0 heavy chain sequence) or SEQ ID NO:9 (KYK2.0 heavy chain sequence). In more preferred embodiments the heavy chain has 100% identity to SEQ ID NO:1 (KYK1.0 heavy chain sequence) or SEQ ID NO:9 (KYK2.0 heavy chain sequence).

The antibody can be an isolated antibody having specificity for human NKG2D, comprising a light chain having at least 90% identity to a sequence such as SEQ ID NO:2 (KYK1.0 light chain sequence) or SEQ ID NO:10 (KYK2.0 light chain sequence). In other embodiments, the percentage identity can be at least 91%, 92%, 93%, 94%, 95%, 96%, 97%, 98%, or 99%, or even 100%. In preferred embodiments, the light chain has at least 95% identity to SEQ ID NO:2 (KYK1.0 light chain sequence) or SEQ ID NO:10 (KYK2.0 light chain sequence). In more preferred embodiments the light chain has 100% identity to SEQ ID NO:2 (KYK1.0 light chain sequence) or SEQ ID NO:10 (KYK2.0 light chain sequence).

In some embodiments, the antibody can comprise any heavy chain as described above, in combination with any suitable light chain, such as those described above. Likewise, the antibody can comprise any of the light chains as described above in combination with any suitable heavy chain, such as those described above. For example, in preferred embodiments, the antibody comprises a heavy chain having at least 90% identity to SEQ ID NO:1 and the light chain has at least 90% identity to SEQ ID NO:2. As another example, the antibody comprises a heavy chain having at least 90% identity to SEQ ID NO:9 and a light chain having at least 90% identity to SEQ ID NO:10. In another preferred embodiment, the antibody comprises the heavy chain of SEQ ID NO:1 and the light chain of SEQ ID NO:2. In a most preferred embodiment, the antibody comprises the heavy chain of SEQ ID NO:9 and the light chain of SEQ ID NO:10.

In addition to a heavy chain as described above, the antibody can further comprise a light chain selected from a Fab library using sequential naive chain shuffling. Likewise, in addition to a light chain as described above, the antibody can further comprise a heavy chain selected from a Fab library using sequential naive chain shuffling.

In other embodiments, the invention provides an isolated antibody, having specificity for human NKG2D, comprising at least one CDR having a sequence selected from the group consisting of SEQ ID NO:3 (KYK-1.0 CDRH1), SEQ ID NO:4 (KYK-1.0 CDRH2), SEQ ID NO:5 (KYK-1.0 CDRH3), SEQ ID NO:6 (KYK-1.0 CDRL1), SEQ ID NO:7 (KYK-1.0 CDRL2), SEQ ID NO:8 (KYK-1.0 CDRL3), SEQ ID NO:11 (KYK-2.0 CDRH1), SEQ ID NO:12 (KYK-2.0 CDRH2), SEQ ID NO:13 (KYK-2.0 CDRH3), SEQ ID NO:14 (KYK-2.0 CDRL1), SEQ ID NO:15 (KYK-2.0 CDRL2), and SEQ ID NO:16 (KYK-2.0 CDRL3). In preferred embodiments, the antibody comprises at least one CDR3 sequence selected from the group consisting of SEQ ID NO:5 (KYK-1.0 CDRH3), SEQ ID NO:8 (KYK-1.0 CDRL3), SEQ ID NO:13 (KYK-2.0 CDRH3) and SEQ ID NO:16 (KYK-2.0 CDRL3). In more preferred embodiments, the antibody comprises two CDR3 sequences such as SEQ ID NO:5 (KYK-1.0 CDRH3) and SEQ ID NO:8 (KYK-1.0 CDRL3), or SEQ ID NO:13 (KYK-2.0 CDRH3) and SEQ ID NO:16 (KYK-2.0 CDRL3).

The antibody can be any antibody including full length antibodies or antibody fragments. For example, the antibody can be any antibody, including without limitation IgA1, IgA2, IgD, IgE, IgG1, IgG2, IgG3, IgG4, and IgM. The antibody can also be any antibody fragment, such as F(ab)2, Fv, scFv, IgGΔCH$_2$, F(ab')2, scFv2CH3, F(ab), VL, VH, scFv4, scFv3, scFv2, dsFv, Fv, scFv-Fc, (scFv)2, a diabody, and a bivalent antibody. The antibody can be any IgG such as IgG1, IgG2, IgG3, IgG4, or synthetic IgG. The antibody can be any modified or synthetic antibody, including non-depleting IgG antibodies or other Fc or Fab variants of antibodies. In a preferred embodiment, the antibody is a Fab.

The antibody or antibody fragment can be produced using any suitable eukaryotic expression system. In a preferred embodiment, the antibody or antibody fragment is produced using a mammalian expression system. In certain embodiments, the heavy chain can be encoded by a DNA sequence such as SEQ ID NO:18 or SEQ ID NO:20, while the light chain can be encoded by a DNA sequence such as SEQ ID NO:17 or SEQ ID NO:19. In a preferred embodiment, the antibody is encoded by a DNA sequence comprising the light chain of SEQ ID NO:17 and the heavy chain of SEQ ID NO:18. In a more preferred embodiment, the antibody is encoded by a DNA sequence comprising the light chain of SEQ ID NO:19 and the heavy chain of SEQ ID NO:20.

In some embodiments, the antibody has specificity for one or more antigens in addition to NKG2D. For example, the antibody can have specificity for a tumor antigen or an antigen associated with a infectious disease.

The antibody can be conjugated to a synthetic molecule using any type of suitable conjugation. It is particularly preferred to use incorporated selenocysteine as described in PCT/US2008/59135, which is incorporated herein by reference. However, other methods of conjugation can also be used such as covalent coupling to native or engineered lysine side-chain amines or cysteine side-chain thiols (See, e.g., Wu et al., *Nat. Biotechnol.* 23: 1137-1146 (2005)). The synthetic molecule can be any molecule such as an agent for targeting a tumor antigen or an infectious disease antigen. Of course, it will be understood that the synthetic molecule also can be a protein or an antibody.

In another embodiment, the invention provides a method of treating a disease or condition in a subject comprising administering a therapeutically effective amount of an isolated antibody as described above to the subject.

In some embodiments, the disease or condition is an autoimmune disease or condition. The autoimmune disease or condition can be any autoimmune disease or condition such as multiple sclerosis, rheumatoid arthritis, type I diabetes mellitus, Crohn's disease, ulcerative colitis, myasthenia gravis, systemic lupus erythematosus, scleroderma, ankylosing spondylitis, graft versus host disease, organ transplantation, Sjögren's syndrome, or autoimmune hepatitis. The antibody can be any antibody as described above. In preferred embodiments, the antibody can be F(ab)2, Fv, scFv, IgGΔCH$_2$, F(ab')2, scFv2CH3, F(ab), VL, VH, scFv4, scFv3, scFv2, dsFv, Fv, (scFv)2, or a synthetic IgG. In a particularly preferred embodiment, the antibody is an Fab.

In other embodiments, the disease or condition is cancer. The cancer can be any cancer including without limitation hematologic malignancies or solid malignancies. Hematologic malignancies can include disorders such as leukemias, lymphomas, myelomas, and NK cell malignancies. Solid malignancies can include cancers of the breast, lung, liver, colon, pancreas, kidney, ovary, head and neck, cervix, stomach, bladder, or other tumor-forming cancers. The antibody can be any antibody described above. In preferred embodiments, the antibody can be an IgG, an scFv, a dsFv, a F(ab')$_2$, a diabody, or a bivalent antibody. In a preferred embodiment, the antibody has specificity for a tumor antigen. In another preferred embodiment, the antibody is conjugated to a synthetic molecule as described above.

In still other embodiments, the disease or condition is an infectious disease. The infectious disease can have any origin such as viral, bacterial, or fungal. The antibody can be any antibody described above. In preferred embodiments, the antibody can be an IgG, an scFv, a dsFv, a F(ab')$_2$, a diabody, or a bivalent antibody. In a preferred embodiment, the antibody has specificity for an antigen of the infectious disease. In another preferred embodiment, the antibody is conjugated to a synthetic molecule as described above.

The invention also provides a composition comprising an isolated antibody as described above and a pharmaceutically acceptable excipient. It will be understood that compositions can be prepared from any of the antibodies described herein. However, a particularly preferred composition comprises an antibody having SEQ ID NO:10 (KYK2.0 light chain sequence) and/or SEQ ID NO:9 (KYK2.0 heavy chain sequence).

The composition of the invention comprises a carrier for the antibody, desirably a pharmaceutically acceptable carrier. The pharmaceutically acceptable carrier can be any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient. The term "carrier" denotes an organic or inorganic ingredient, natural or synthetic, with which the active ingredient is combined to facilitate the application. The pharmaceutically acceptable carrier can be co-mingled with one or more of active components, e.g., the hybrid molecule, and with each other, when more than one pharmaceutically acceptable carrier is present in the composition in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

The pharmaceutical composition can be presented in unit dosage form and can be prepared by any suitable method, many of which are well known in the art of pharmacy. Such methods include the step of bringing the active agent into association with a carrier that constitutes one or more accessory ingredients. In general, the composition is prepared by uniformly and intimately bringing the hybrid molecule into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in *Remington's Pharmaceutical Sciences*, Mack Publishing Co., Easton, Pa., which is incorporated herein in its entirety by reference thereto.

The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The following examples further illustrate the invention but, of course, should not be construed as in any way limiting its scope.

Example 1

This example demonstrates the preparation of a human anti-human NKG2D Fab.

To obtain heavy and light chains of a human NKG2D Fab, a naïve human Fab library was prepared. For this, a naïve human Fab library in phage display vector pC3C. The design of pC3C for the generation and selection of Fab libraries with human constant domains was previously reported in Hofer et al., *J. Immunol. Methods* 318: 75-87 (2007).

Freshly harvested bone marrow from 6 healthy donors of diverse age, sex, and ethnicity (Poietics Human Bone Marrow; Cambrex) was separately processed for total RNA preparation and RT-PCR amplification of human $V_\kappa$, $V_\lambda$, and $V_H$ encoding sequences. To include all human germlines, a total of 61 newly designed primers in 186 different and separate combinations were used for each of the 6 healthy donors. Using established protocols as provided in Barbas et al., *Phage Display: A Laboratory Manual*, Cold Spring Harbor Laboratory Press, Cold Spring Harbor, N.Y. (2001), 10 mL bone marrow from each donor was homogenized with PowerGen 125 homogenizer (Thermo Fisher Scientific), and total RNA was extracted with TRI Reagent (Molecular Research Center) and further purified by LiCl precipitation. First-strand cDNA synthesis from total RNA using an oligo(dT) primer and SuperScript III reverse transcriptase (Invitrogen) were carried out according to the manufacturer's protocol. $V_\kappa$, $V_\lambda$, and $V_H$ encoding sequences were separately amplified from each donor's first-strand cDNA by PCR using recombinant Taq DNA polymerase (Fermentas) and combinations of 12 sense/1 antisense primers for $V_\kappa$, 20 sense/3 antisense primers for $V_\lambda$, and 19 sense/6 antisense primers for $V_H$, for a total of 186 different combinations, encompassing all human germlines. The antisense primers for $V_\lambda$ and $V_H$ align to $J_\lambda$ and $J_H$ germlines, respectively, whereas the antisense primer for $V_\kappa$ aligns to the $C_\kappa$ encoding sequence. Three pools combining $V_\kappa$, $V_\lambda$, and $V_H$, respectively, from all donors were generated to increase the complexity of the libraries. Human $C_\kappa$-pelB and $C_\lambda$-pelB encoding sequences required for the $V_\kappa$-$C_\kappa$-$V_H$ and $V_\lambda$-$C_\lambda$-$V_H$ cassette assembly, respectively, were amplified from $pC_\kappa$ (Hofer et al., *J. Immunol. Methods* 318: 75-87 (2007)) and $pC_\lambda$. For the latter, a sequence encoding human $C_\lambda$ (IGLC2; GenBank accession number J00253) was amplified by PCR from human bone marrow and cloned and confirmed analogous to $pC_\kappa$. $V_\kappa$-$C_\kappa$-$V_H$ and $V_\lambda$-$C_\lambda$-$V_H$ cassettes were assembled in one fusion step based on 3-fragment overlap extension PCR, digested with SfiI, and cloned into pC3C as described in Hofer et al., *J. Immunol. Methods* 318: 75-87 (2007).

Cloning into pC3C by asymmetric SfiI ligation resulted in two libraries consisting of approximately $1.0 \times 10^9$ ($\kappa$) and $0.5 \times 10^9$ ($\lambda$) independently transformed human Fab clones, respectively (FIG. 1). Transformation of *E. coli* strain ER2738 (New England Biolabs) by electroporation yielded approximately $1.0 \times 10^9$ and $0.5 \times 10^9$ independent transformants for the $\kappa$ and $\lambda$ phagemid libraries, respectively. Randomly picked independent transformants from each library were analyzed for Fab expression by ELISA and for sequence diversity by DNA fingerprinting as described in Popkov et al., *J. Mol. Biol.* 325: 325-35 (2003). Using VCSM13 helper phage (Stratagene), the phagemid libraries were converted to phage libraries as described in Rader, C., *Methods Mol. Biol.* 525: 101-28 (2009), and stored at 4° C. after adding 0.01 volume 2% (w/v) sodium azide.

Based on established protocols as described in Rader, C., *Methods Mol. Biol.* 525:101-28 (2009), the re-amplified and combined naïve human Fab libraries were selected by 4 rounds of panning against immobilized human Fc-NKG2D (R&D Systems), which is a recombinant fusion protein of human Fc and the extracellular domain (amino acids 78-216) of human NKG2D, or 3 rounds of panning against immobilized tetanus toxoid (TT; prepared from Sanofi Pasteur vaccine formulation by dialysis against PBS). During the panning against immobilized human Fc-NKG2D, polyclonal human IgG (Pierce) was added as decoy at a final concentration of 2.5 µg/µL. Both selections yielded a number of clones that were positive when tested for binding to human Fc-NKG2D or TT by ELISA. Further analyses of these clones by DNA fingerprinting with AluI as well as by DNA sequencing revealed a single repeated $\lambda$ clone (KYK-1.0) from the selection against Fc-NKG2D. By contrast, the selection against TT gave a number of different repeated $\kappa$ clones of which TT11 was pursued to serve as negative control for all subsequent studies. The re-amplified and combined naïve human Fab libraries were also selected by 4 rounds of panning against human Fc-NKG2D in solution, using mouse anti-human IgG1 Fc-specific mAb 10G/2C11 (Meridian Life Science) that was coated onto surface activated magnetic beads (MyOne Tosylactivated Dynabeads; Invitrogen) according to the manufacturer's protocol and used for capturing as described in Rader, C., *Methods Mol. Biol.* 525: 101-28 (2009). Again, KYK-1.0 was selected as single repeated clone.

To identify additional combinations of $V_\lambda$ and $V_H$, affinity maturation of KYK-1.0 was performed sequentially for light chain and heavy chain fragment by naïve chain shuffling (FIG. 2). For the first step, a modified pC3C phagemid, pC3C-Cam, was used in which the ampicillin resistance gene was replaced by the chloramphenicol resistance gene from plasmid pPCR-Script Cam SK(+) (Stratagene). The previously amplified $V_\kappa$ and $V_\lambda$, encoding sequences from all 6 donors were combined with the $V_H$ encoding sequence of KYK-1.0 through $V_\kappa$-$C_\kappa$-$V_H$ and $V_\lambda$-$C_\lambda$-$V_H$ cassette assembly as described for the generation of the naïve human Fab library, digested with SfiI, and cloned into pC3C-Cam. Transformation of *E. coli* strain ER2738 by electroporation yielded approximately $1.5 \times 10^7$ independent transformants for each $\kappa$ and $\lambda$ phagemid libraries. The corresponding phage libraries were selected separately by 3 rounds of panning on immobilized human Fc-NKG2D, yielding a number of repeated $\lambda$ clones, but no $\kappa$ clones, that were positive when tested for binding to human Fc-NKG2D by ELISA and revealed sequence diversity when analyzed by DNA fingerprinting with AluI as well as by DNA sequencing. (These clones were designated KYK-1.N for KYK-1.1, KYK-1.2, KYK-1.3, etc.). For the second step, the $V_\lambda$ encoding sequences of approximately 100 KYK-1.N clones were amplified by PCR and combined with the previously amplified $V_H$ encoding sequences from all 6 donors using $V_\lambda$-$C_\lambda$-$V_H$ cassette assembly and SfiI cloning into the original pC3C phagemid with the ampicillin resistance gene. Transformation of *E. coli* strain ER2738 by electroporation yielded approximately $5 \times 10^8$ independent transformants. The corresponding phage library was selected by 4 rounds of panning on immobilized human Fc-NKG2D, yielding several repeated clones of which one, designated KYK-2.0, was dominating as revealed by DNA fingerprinting with AluI and DNA sequencing. KYK-2.0 also gave the strongest signal when tested for binding to human Fc-NKG2D by ELISA.

To remove the gene III fragment of pC3C (FIG. 1) and add a C-terminal (His)$_6$ tag, the expression cassettes encoding KYK-1.0, KYK-2.0, and TT11 Fab were transferred by SfiI cloning into pC3C-His as described in Kwong et al., *Curr Protoc Protein Sci* 6:10 (February 2009). Following transformation into *E. coli* strain XL1-Blue (Stratagene) and expression through IPTG induction, KYK-1.0, KYK-2.0, and TT11 Fab were purified from culture supernatants by IMAC. The quality and quantity of purified Fab was determined by SDS-PAGE and A$_{280}$ absorbance.

Shown in FIG. 3 are the amino acid sequences of the variable domains of V$_\lambda$ and V$_H$ of KYK-1.0 and KYK-2.0 aligned with their corresponding human germlines based on IgBLAST analysis (www.ncbi.nlm.nih.gov/igblast/). The FR1-FR3 regions of V$_H$ of KYK-1.0 and KYK-2.0 are well conserved with respect to their shared V gene VH 3-30 and among each other. By contrast, the FR1-FR3 regions of V$_\lambda$ of KYK-1.0 and KYK-2.0 are highly divergent, are derived from different V gene classes (Vλ3-21 and Vλ1-36, respectively), and contain more somatic hypermutations. Second, the CDR3 regions from both V$_\lambda$ (LCDR3) and V$_H$ (HCDR3) of KYK-1.0 and KYK-2.0 are highly divergent. The HCDR3 region of KYK-2.0 is 3 amino acids longer than the HCDR3 region of KYK-1.0, indicating a different HCDR3 conformation. Third, V$_\lambda$ of KYK-1.0 contains 3 clusters with negatively charged amino acids in CDR1 (GGDDIETKSVH (SEQ ID NO:6)), CDR2 (DDDDRPS (SEQ ID NO:7)), and CDR3 (QVWDDNNDEWV (SEQ ID NO:8)). It is thought that these negatively charged clusters promote binding to the highly positively charged NKG2D dimer interface that mediates ligand binding (Wolan et al., *Nat. Immunol.* 2, 248-54 (2001)). The affinity maturation from KYK-1.0 to KYK-2.0 diminished these negatively charged clusters.

Taken together, this sequential naïve chain shuffling procedure provides a related, yet substantially divergent solution for human NKG2D binding that (i) was not present in the original naïve human Fab library, (ii) would have been missed by focused affinity maturation strategies such as CDR walking as described in Hoogenboom, H. R., *Nat. Biotechnol.* 23: 1105-16 (2005) and Rader, C., *Drug Discov. Today* 6: 36-43 (2001), and (iii) in contrast to other directed evolution strategies for affinity maturation as described in Hoogenboom, H. R., *Nat. Biotechnol.* 23: 1105-16 (2005) and Rader, C., *Drug Discov. Today* 6: 36-43 (2001), sequential naïve chain shuffling does not further deviate from human germlines, thereby preserving low immunogenicity.

Example 2

This example demonstrates the affinity and specificity of KYK-1.0 and KYK-2.0 Fab.

KYK-1.0, KYK-2.0, and TT11 Fab were recombinantly equipped and expressed with a C-terminal $(His)_6$ tag using *Escherichia coli* expression vector pC3C-His[19] and purified by immobilized metal ion affinity chromatography (IMAC). ELISA on immobilized proteins was then used as a first assessment of the specificity of purified KYK-1.0 and KYK-2.0 Fab. The following proteins were used for coating: Human Fc-NKG2D, mouse Fc-NKG2D, human CD22-Fc, human ULBP2-Fc (all from R&D Systems), human CD23 (Lab Vision Corporation), tetanus toxoid (Sanofi-Pasteur), and human Fc-ROR1 (Baskar et al., *Clin. Cancer Res.* 14: 396-404 (2008)). Using 100 ng of protein for coating, ELISA was carried out as described in Hofer et al., *J. Immunol. Methods* 318: 75-87 (2007). Goat-anti-human Fab polyclonal antibodies conjugated to horseradish peroxidase were used for detection. The absorbance at 405 nm was read before the signal obtained for KYK-2.0 Fab on immobilized human NKG2D reached saturation. The signal obtained for KYK-1.0 Fab on immobilized human NKG2D increased further relative to background after longer exposure (data not shown).

As shown in FIG. 4, both KYK-1.0 and KYK-2.0 Fab bound human NKG2D but neither mouse NKG2D nor a panel of other proteins that were tested in parallel. The lack of species cross-reactivity of both KYK-1.0 and KYK-2.0 was expected as human and mouse NKG2D only share 60% amino acid sequence identity. The ELISA also indicated a substantially higher affinity of the evolved KYK-2.0 Fab compared to the original KYK-1.0 Fab. The control Fab, TT11, revealed specific binding to tetanus toxoid (FIG. 4).

For quantitative analysis of the thermodynamic and kinetic binding properties, the interaction of KYK-1.0 and KYK-2.0 Fab, respectively, with human NKG2D was analyzed by surface plasmon resonance using a BIAcore 2000 instrument. Surface plasmon resonance for the measurement of the affinity of KYK-1.0 and KYK-2.0 Fab and the virtual affinity (avidity) of KYK-1.0 and KYK-2.0 IgG1 as well as mouse anti-human NKG2D mAbs 149810 (R&D Systems) and 1D11 (BD Biosciences) to human Fc-NKG2D (R&D Systems) was performed as described in Hofer et al., *J. Immunol. Methods* 318: 75-87 (2007) except for using 20 mM NaOH (instead of 25 mM HCl) for regeneration. These results are presented in Table 1.

TABLE 1

Analysis of KYK-1.0 and KYK-2.0 Fab and IgG1 binding to human NKG22D by surface plasmon resonance using a BIAcore 200 instrument.

| | $k_{on}$ ($\times 10^5$ $M^{-1}s^{-1}$) | $k_{off}$ ($\times 10^{-2}$ $s^{-1}$) | $k_d$ (nM) |
|---|---|---|---|
| KYK-1.0 Fab | 14.0 | 3.7 | 27 |
| KYK-1.0 IgG1 | 3.1 | 0.056 | 1.8* |
| KYK-2.0 Fab | 7.4 | 0.43 | 5.8 |
| KYK-2.0 IgG1 | 3.2 | 0.012 | 0.38* |
| 149810 | 1.4 | 0.0051 | 0.36* |
| 1D11 | 0.4 | 0.0029 | 0.73* |

Human NKG2D was immobilized on the sensor chip.
Association ($k_{on}$) and dissociation ($k_{off}$) rate constants were calculated using BIA evaluation software.
The equilibrium dissociation constant ($K_d$) was calculated from $k_{off}/k_{on}$.
The "*" values for all IgG1 reflect bivalent rather than monovalent binding.

The affinities ($K_d$) were measured as 27 nM for KYK-1.0 Fab and 5.8 nM for KYK-2.0 Fab, demonstrating a ~4.5 fold overall improvement following affinity maturation. The affinity of KYK-1.0 Fab is well within the range of affinities obtained for naïve human and synthetic human Fab libraries that are more than 10 times larger in terms of number of independent Fab clones (See, e.g., Griffiths et al., *EMBO J.* 13: 3245-60 (1994), de Haard et al., *J. Biol. Chem.* 274: 18218-30 (1999), Rothe et al., *J. Mol. Biol.* 376: 1182-200 (2008)). The higher affinity of KYK-2.0 Fab was solely mediated by a ~8.5 fold slower dissociation compared to KYK-1.0 Fab, an expected result for the $k_{off}$ driven selection methodology applied. KYK-1.0 Fab revealed an extraordinarily fast association with a $k_{on}$ of $1.4\times10^6$ $M^{-1}$ $s^{-1}$ (Table 1) as compared with chimeric rabbit/human Fab from immune libraries (See, e.g., Hofer et al., *J. Immunol. Methods* 318: 75-87 (2007), Popkov et al., *J. Mol. Biol.* 325: 325-35 (2003)) and human Fab evolved by CDR walking (see Rader et al., *FASEB J.* 16: 2000-2 (2002). In general, the selection of a $k_{on}$ that exceeds 1×10⁶ M⁻¹ s⁻¹ has been confined to Fab that were derived from synthetic human libraries and further improved by affinity maturation (Lee et al., *J. Mol. Biol.* 340: 1073-93 (2004)). The association of KYK-1.0 Fab is thought to be driven by electrostatic attraction between the negatively charged clusters of KYK-1.0 Fab and the positively charged interface of the NKG2D dimer, because the affinity maturation from KYK-1.0 to KYK-2.0 Fab not only diminished the negatively charged clusters but also reduced the $k_{on}$ despite a gain in affinity (Table 1).

To confirm this observation, the interaction of KYK-2.0 Fab and human NKG2D was analyzed using quartz crystal microbalance using an Attana A100 instrument. Under various conditions, KYK-2.0 Fab revealed a $k_{on}$ of 4.5-8.9×10⁵ M⁻¹ s⁻¹ and a $k_{off}$ of 1.2-1.8×10⁻³ s⁻¹, resulting in an affinity of 1.9-3.0 nM. Thus, surface plasmon resonance and quartz crystal microbalance measurements gave fairly consistent thermodynamic and kinetic binding data for the interaction of KYK-2.0 Fab and human NKG2D.

The interaction of KYK-1.0 and KYK-2.0 Fab with the positively charged interface of the NKG2D dimer, which is highly conserved between mouse and human NKG2D and implicated in NKG2D ligand binding (See, e.g., Wolan et al., *Nat. Immunol.* 2, 248-54 (2001), Li et al., *Nat. Immunol.* 2: 443-51 (2001), Li et al., *Immunity* 16: 77-86 (2002)), indicates that the selected antibodies interfere with NKG2D receptor/ligand interactions.

To confirm this observation, HEK 293F cells stably expressing human NKG2D were generated, and HEK 293F cells stably expressing human ROR1 (Baskar et al., *Clin. Cancer Res.* 14: 396-404 (2008)) were generated as a negative control.

Full-length human NKG2D cDNA, kindly provided by Dr. Charles L. Sentman, and full-length human ROR1 cDNA (OriGene) were cloned into mammalian expression vector pIRES2-EGFP (Clontech; with neomycin resistance gene) downstream of CMV promoter and upstream of IRES. The resulting plasmids were transfected into HEK 293F cells with 293fectin (Invitrogen) using conditions detailed in the manufacturer's protocol. Mammalian expression vector pCMV6-XL5 containing the full-length cDNA of human DAP10 under the control of a CMV promoter (OriGene; without neomycin resistance gene) was co-transfected (1:1) to permit cell surface expression of human NKG2D. The transfected cells were maintained in 25-cm³-flasks in plain FreeStyle serum-free medium (Invitrogen) supplemented with 200 µg/mL G418 (Invitrogen). Subsequently, attached cells were transferred to fresh flasks and expanded in plain FreeStyle serum-free medium. Flow cytometry revealed that >90% of the cells expressed EGFP. Fluorescent cells were further purified by FACS using a FACSVantage SE DiVa instrument (BD Biosciences), expanded in plain FreeStyle serum-free medium, and transferred in Recovery Cell Culture Freezing Medium (Invitrogen) for cryopreservation in liquid nitrogen. Freshly thawed HEK 293F/human NKG2D and HEK 293F/human ROR1 cells were recovered and expanded in plain FreeStyle serum-free medium prior to subsequent experiments.

ELISA was performed on the resulting whole cells. In a 96-well tissue culture plate (Corning), 4×10⁵ stably transfected HEK 293F/human NKG2D or HEK 293F/human ROR1 cells were incubated with 2 µg KYK-1.0 Fab, KYK-2.0 Fab, TT11 Fab, mouse anti-human NKG2D mAb 149810, or no antibody in 2% (v/v) nonimmune goat serum (Jackson ImmunoResearch Laboratories) in PBS for 1 h on ice. Subsequently, 100 ng of human MICA-Fc, human MICB-Fc, and human ULBP2-Fc (all from R&D Systems) were added to the cells and incubated for 1 h on ice. After washing twice with PBS through centrifugation at 500 g for 5 min at 4° C., the cells were incubated with a 1:3000 dilution of biotinylated goat anti-human Fc polyclonal antibodies (Jackson ImmunoResearch Laboratories) in 2% (v/v) nonimmune goat serum in PBS for 1 h on ice. Subsequently, after washing twice with PBS as before, the cells were incubated with a 1:3000 dilution of HRP-coupled streptavidin (BD Biosciences) in 2% (v/v) nonimmune goat serum in PBS for 30 min on ice. After washing twice with PBS as before, HRP substrate 2,2'-azino-bis(3-ethyl-benzthiazoline)-6-sulfonic acid (Roche) was prepared and added according to the manufacturer's directions and incubated at room temperature until a green color developed (5-10 min). The cells were spun down as before, and the supernatants were transferred to a 96-well ELISA plate to measure the absorbance at 405 nm in a VersaMax microplate reader (Molecular Devices).

As shown in FIG. 5, KYK-2.0 Fab blocked the binding of all three human NKG2D ligands as potently as the commercially available mouse anti-human NKG2D mAb 149810 in IgG format. By contrast, KYK-1.0 Fab was less potent, and TT11 Fab did not reveal any blocking activity.

These results show that both KYK-1.0 Fab and KYK-2.0 Fab have blocking activity against NKG2D ligands, although KYK-2.0 Fab has stronger activity than KYK-1.0 Fab.

Example 3

This example demonstrates the affinity and specificity of KYK-2.0 IgG1.

For the expression of fully human KYK-1.0 IgG1λ, KYK-2.0 IgG1λ, and TT11 IgG1κ, the $V_H$ and light chain encoding sequences were PCR amplified using appropriately designed primers and cloned into mammalian expression vector PIGG as described in Hofer et al., *J. Immunol. Methods* 318: 75-87 (2007). Using 293fectin, 300 µg of PIGG-KYK-1.0, PIGG-KYK-2.0, or PIGG-TT11 plasmids were transiently transfected into 3×10⁸ HEK 293F cells and kept in 300 mL FreeStyle serum-free medium in a 500-mL spinner flask on a stirring platform at 75 rpm (CELLSPIN System; Integra) in a humidified atmosphere containing 8% CO₂ at 37° C. After 4 days, the medium was collected after centrifugation, replaced for an additional 3-4 days, and collected again. Pooled supernatants were then processed and purified using 1-mL recombinant Protein A or Protein G HiTrap columns (GE Healthcare) as described in Hofer et al., *J. Immunol. Methods* 318: 75-87 (2007). The quality and quantity of purified IgG1 was determined by SDS-PAGE and $A_{280}$ absorbance.

KYK-1.0 and KYK-2.0 IgG1 revealed a strong improvement in virtual affinity as measured by surface plasmon resonance (Table 1). KYK-2.0 IgG1 and mouse anti-human NKG2D mAbs 149810 and 1D11 revealed similar virtual affinities in the subnanomolar range (Table 1). Additional studies based on surface plasmon resonance indicated that KYK-2.0, 149810, and 1D11 recognize three distinct but partially overlapping epitopes displayed by the extracellular domain of human NKG2D.

To confirm and further assess the specificity of KYK-2.0 IgG1, its binding to human peripheral blood mononuclear cells (PBMC) subpopulations was analyzed by flow cytometry and compared to mouse anti-human NKG2D mAb 149810 (positive control) and TT11 IgG1 (negative control).

Purified KYK-2.0 and TT11 IgG1 were biotinylated using the BiotinTag Micro-Biotinylation Kit (Sigma-Aldrich). Human PBMC were prepared from freshly drawn whole blood of healthy donors obtained from the Department of Transfusion Medicine at the NIH by density gradient separation on lymphocyte separation medium (ICN Biochemicals) and kept on ice in undiluted human AB serum (Invitrogen) for 15 min to block Fcγ receptors. Blocked PBMC were diluted to $5 \times 10^5$ cells in 10% (v/v) human AB serum in PBS and incubated with 10 µg/mL biotinylated KYK-2.0 or TT11 IgG1 for 1 h on ice in a total volume of 50 µL. After washing twice with 2% (v/v) human AB serum in PBS, the cells were incubated with 2 µg/mL PE-coupled streptavidin (BD Biosciences) and APC-coupled co-staining mAbs (see below) for 30 min on ice, washed twice as before, and resuspended in 400 µL 2% (v/v) human AB serum in PBS. PBMC subpopulations were gated by co-staining with APC-coupled mouse anti-human CD4, CD8, CD16, CD19, and CD56 mAbs (all from BD Biosciences), and 7-aminoactinomycin D (7-AAD; Invitrogen) was added to exclude dead cells from the analysis. PE-coupled mouse anti-human NKG2D mAb 149810 (R&D Systems) was used as positive control. Flow cytometry was performed using a FACSCalibur instrument (BD Biosciences) and analyzed using CellQuest software (BD Biosciences).

Revealing essentially identical specificities for human T cells and NK cells, KYK-2.0 IgG1 and 149810 bound to the majority of human CD8+, CD16+, and CD56+ cells as well as to a small fraction of human CD4+ cells (FIG. 6). Human B cells (CD19+) were not bound by either antibody, and TT11 IgG1 was negative for all human PBMC subpopulations.

These results show that KYK-2.0 IgG1 is capable of selectively recognizing human lymphocytes known to express NKG2D.

Example 4

This example demonstrates the dual antagonistic and agonistic activity of KYK-1.0 and KYK-2.0 IgG1.

To test the antagonizing activity of KYK-2.0 IgG1 in solution, an ex vivo expansion protocol was prepared based on IL-15, IL-15Rα, and 4-1BBL that was formulated to increase the cytolytic activity of human NK cells. Human PBMC were prepared from whole blood as described above. Human NK cells (CD16+ CD56+) were negatively selected and purified from human PBMC by magnetic activated cell sorting (MACS) using the NK Cell Isolation Kit (Miltenyi Biotec). The purity of the selection was greater than 95%. Expansion was carried out for 1 week in the presence of 10 ng/mL recombinant human IL-15 (PeproTech) and artificial antigen presenting cells (aAPCs) (See, e.g., Zhang et al., *J. Immunol* 179, 4910-8 (2007)) expressing human 4-1BBL and human IL-15Rα at a ratio of 1-2 to 1 (cell line 2D11; H. Z. and C. L. M., manuscript in preparation). The cytolytic activity of purified human NK cells as effector cells before or after expansion was tested in a conventional $^{51}$Cr release assay using human cell lines K562 and Daudi (American Type Culture Collection) as target cells. Briefly, target cells (T) were radiolabeled with Na$^{51}$CrO$_4$ (PerkinElmer) for 1 h at 37° C. and 5% CO$_2$, then washed and co-incubated with effector cells (E) in 96-well U-bottomed plates at an E/T ratio of 40:1 in triplicates of 5,000 target cells/well. To test the blockade of cytolytic activity, KYK-2.0 IgG1, TT11 IgG1 (negative control), and mouse anti-human NKG2D mAb 149810 (positive control) were added to a final concentration of 20 µg/mL. After 4 h at 37° C. and 5% CO$_2$, supernatants were collected and counted in a gamma counter (PerkinElmer). The percent of specific lysis was calculated as follows: (experimental release minus spontaneous release) times 100 divided by (maximum release minus spontaneous release). Maximum release was determined through lysis in the presence of 0.1 N HCl.

When compared for their cytolytic activity toward human chronic myelogenous leukemia (CML) cell line K562, a classical NK cell target expressing NKG2D ligands and not expressing MHC class I ligands, ex vivo expanded human NK cells revealed twice the activity measured for fresh human NK cells (FIG. 7). In contrast to TT11 IgG1, both KYK 2.0 IgG1 and mouse anti-human NKG2D mAb 149810 significantly blocked this increase in cytolytic activity. Remarkably, the ex vivo expanded human NK cells also exhibited substantial cytolytic activity toward human Burkitt's lymphoma cell line Daudi (FIG. 7). Like K562 cells, Daudi cells express NKG2D ligands and do not express MHC class I ligands. Unlike K562 cells, however, Daudi cells are known to be resistant to fresh human NK cells which was confirmed (FIG. 7). Again, KYK 2.0 IgG1 and mouse anti-human NKG2D mAb 149810, but not TT11 IgG1, were found to significantly block the acquired cytolytic activity of ex vivo expanded human NK cells.

These findings demonstrated that soluble KYK-2.0 IgG1 exhibits antagonistic activity through interfering with effector cell to target cell recognition mediated by NKG2D receptor/ligand interactions. The degranulation markers CD107a and CD107b which correlate with NK cell cytotoxicity (See, e.g., Alter et al., *J. Immunol Methods* 294: 15-22 (2004), Betts et al., *Methods Cell Biol.* 75, 497-512 (2004)) were used to determine whether the agonizing activity of target cell surface NKG2D ligands can be mimicked by immobilized KYK-2.0 IgG1.

KYK-2.0 IgG1, in parallel to TT11 IgG1, mouse anti-human NKG2D mAb 149810, and nonspecific polyclonal mouse IgG, was coated on a 24-well tissue culture plate and incubated with IL-2 stimulated human PBMC from 4 different healthy donors. Subsequently, the percentage of degranulated NK cells (CD56+ CD107a/CD107b+) among total NK cells (CD56+) was quantified by flow cytometry (FIG. 8 and Table 2).

TABLE 2

| Activation of human NK cells by KYK-2.0 IgG1 crosslinking | | | | |
|---|---|---|---|---|
| | Donor 1 | Donor 2 | Donor 3 | Donor 4 |
| PBS | 2.6% | 2.9% | 16.8% | 6.0% |
| KYK-2.0 IgG1 | 24.5% | 27.9% | 48.0% | 25.5% |
| TT11 IgG1 | 2.4% | 5.1% | 16.8% | 5.4% |
| 149810 | 13.6% | 16.3% | 24.3% | 8.4% |
| Mouse IgG | 2.2% | 5.2% | 13.4% | 4.5% |

Human PBMC from 4 different healthy donors were prepared from whole blood as described above or from leukocytes collected by apheresis and were cultured in IMDM medium (Invitrogen) supplemented with 10% (v/v) human AB serum (Invitrogen), penicillin/streptomycin, and 100 U/mL IL-2 (PeproTech) at a density of $2 \times 10^6$ cells/mL for 4-10 days before the experiment. Every 3-4 days, half of the culture medium was replaced with fresh medium. One day before the experiment, a 24-well tissue culture plate was coated with 500 µL/well of 5 µg/mL KYK-2.0 IgG1, TT11 IgG1, mouse anti-human NKG2D mAb 149810, or nonspecific polyclonal mouse IgG (Jackson ImmunoResearch Laboratories) in PBS at 4° C. overnight. After washing 3 times with PBS, $1 \times 10^6$ cells of the non-adherent fraction of the prepared PBMC diluted in 1 mL of the same medium plus 0.67 µL GolgiStop (BD Biosciences; a protein transport inhibitor containing monensin) were added to each well and incubated for 3 h at 37° C. and 5% CO$_2$. Subsequently, the cells were stained with a mixture of FITC-coupled mouse anti-human CD107a and mouse anti-human CD107b mAbs (BD Biosciences) to measure degranulation. NK cells were gated by co-staining with APC-coupled mouse anti-human CD56 mAb, and dead cells were gated out by 7-AAD co-staining. As before, flow cytometry was performed using a FACSCalibur instrument and analyzed using CellQuest software.

Whereas the percentage of degranulated NK cells did not increase following incubation with immobilized TT11 IgG1, KYK-2.0 IgG1 potently induced NK cell degranulation in PBMC from all 4 different healthy donors. Mouse anti-human NKG2D mAb 149810 had been previously shown to exhibit agonistic activity in a redirected cross-species lysis assay with cell line P815 as target cells (mouse FcγR+) and human cell line NKL as effector cells (human NKG2D+) (Ehrlich et al., *J. Immunol.* 174: 1922-31 (2005)). The agonistic activity of mouse anti-human NKG2D mAb 149810 was confirmed in the degranulation assay by comparison with nonspecific polyclonal mouse IgG. Notably, despite matching avidities (Table 1) and indistinguishable antagonistic activities (FIG. 7), KYK-2.0 IgG1 was found to exhibit substantially stronger agonistic activity than mouse anti-human NKG2D mAb 149810 (FIG. 8 and Table 2).

These results confirm that soluble KYK-2.0 IgG1 exhibits antagonistic activity through interfering with effector cell to target cell recognition mediated by NKG2D receptor/ligand interactions, and furthermore that the agonizing activity of target cell surface NKG2D ligands can be mimicked by immobilized KYK-2.0 IgG1.

Example 5

This example demonstrates use of an NKG2D antibody in treating autoimmune disease.

KYK-2.0 Fab is prepared as described above and formulated in an aqueous composition. The composition is administered intravenously in one or more doses to a test cohort of patients suffering from an autoimmune disease, such as type 1 diabetes mellitus. A control cohort is administered saline intravenously in a corresponding dosage regimen.

The test cohort shows improvement in one or more clinical indicators associated with the autoimmune disease.

These results demonstrate that NKG2D antibody treatment is useful in treating autoimmune disease.

Example 6

This example demonstrates use of an NKG2D antibody in treating cancer.

KYK-2.0 IgG1 is prepared as described above and formulated in an aqueous composition. The composition is administered intravenously in one or more doses to a test cohort of patients suffering from cancer, such as myeloma. A control cohort is administered saline intravenously in a corresponding dosage regimen.

The test cohort shows improvement in one or more clinical indicators associated with the cancer.

These results demonstrate that NKG2D antibody treatment is useful in treating cancer.

Example 7

This example demonstrates use of an NKG2D antibody in treating infectious disease.

KYK-2.0 IgG1 is prepared as described above and formulated in an aqueous composition. The composition is administered intravenously in one or more doses to a test cohort of patients suffering from an infectious disease, such as hepatitis A control cohort is administered saline intravenously in a corresponding dosage regimen.

The test cohort shows improvement in one or more clinical indicators associated with the infectious disease.

These results demonstrate that NKG2D antibody treatment is useful in treating infectious disease.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antibody having specificity for human NKG2D, comprising the following complementarity determining regions (CDRs): SEQ ID NO:11 (CDRH1), SEQ ID NO:12 (CDRH2), SEQ ID NO:13 (CDRH3), SEQ ID NO:14 (CDRL1), SEQ ID NO:15 (CDRL2), and SEQ ID NO:16 (CDRL3).

2. The antibody of claim 1 comprising:
  (a) a heavy chain having at least 90% identity to the amino acid sequence of SEQ ID NO:9; and
  (b) a light chain having at least 90% identity to the amino acid sequence of SEQ ID NO:10.

3. The antibody of claim 2, wherein the heavy chain has at least 95% identity to the amino acid sequence of SEQ ID NO:9.

4. The antibody of claim 2, wherein the heavy chain has the amino acid sequence of SEQ ID NO:9.

5. The antibody of claim 2, wherein the light chain has at least 95% identity to the amino acid sequence of SEQ ID NO:10.

6. The antibody of claim 2, wherein the light chain has the amino acid sequence of SEQ ID NO:10.

7. The antibody of claim 1, wherein the antibody is selected from the group consisting of IgA1, IgA2, IgD, IgE, IgG1, IgG2, IgG3, IgG4, IgM, F(ab)2, Fv, scFv, IgGΔCH2, F(ab')2, scFv2CH3, F(ab), VL, VH, scFv4, scFv3, scFv2, dsFv, Fv, scFv-Fc, (scFv)2, a non-depleting IgG, a diabody, and a bivalent antibody.

8. The antibody of claim 7, wherein the antibody is an IgG selected from the group consisting of IgG1, IgG2, IgG3, IgG4, and synthetic IgG.

9. The antibody of claim 7, wherein the antibody is a Fab.

10. The antibody of claim 7, wherein the antibody has specificity for a tumor antigen.

11. The antibody of claim 7, wherein the antibody is conjugated to a synthetic molecule.

12. The antibody of claim 11, wherein the synthetic molecule is an antibody.

13. A composition comprising the antibody of claim 1, and a pharmaceutically acceptable excipient.

14. A conjugate comprising the antibody of claim 1.

15. The conjugate of claim 14, further comprising (i) an agent for targeting a tumor antigen or an infectious disease antigen, (ii) a protein, or (iii) an antibody.

16. An antibody having specificity for human NKG2D comprising a light chain having the amino acid sequence of SEQ ID NO:10 and a heavy chain having the amino acid sequence of SEQ ID NO:9.

* * * * *

SEQUENCE LISTING

<160> NUMBER OF SEQ ID NOS: 20

<210> SEQ ID NO 1
<211> LENGTH: 118
<212> TYPE: PRT

-continued

<213> ORGANISM: Homo sapiens

<400> SEQUENCE: 1

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Lys Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
            100                 105                 110

Leu Val Thr Val Ser Ser
            115

<210> SEQ ID NO 2
<211> LENGTH: 108
<212> TYPE: PRT
<213> ORGANISM: Homo sapiens

<400> SEQUENCE: 2

Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
                85                  90                  95

Trp Val Phe Gly Gly Gly Thr Gln Leu Thr Val Leu
            100                 105

<210> SEQ ID NO 3
<211> LENGTH: 5
<212> TYPE: PRT
<213> ORGANISM: Homo sapiens

<400> SEQUENCE: 3

Ser Tyr Gly Met His
1               5

<210> SEQ ID NO 4
<211> LENGTH: 17
<212> TYPE: PRT
<213> ORGANISM: Homo sapiens

<400> SEQUENCE: 4

Phe Ile Arg Tyr Asp Gly Ser Asn Lys Tyr Tyr Ala Asp Ser Val Lys
1               5                   10                  15

Gly

<210> SEQ ID NO 5
<211> LENGTH: 9
<212> TYPE: PRT
<213> ORGANISM: Homo sapiens

<400> SEQUENCE: 5

Asp Arg Phe Gly Tyr Tyr Leu Asp Tyr
1               5

<210> SEQ ID NO 6
<211> LENGTH: 11
<212> TYPE: PRT
<213> ORGANISM: Homo sapiens

<400> SEQUENCE: 6

Gly Gly Asp Asp Ile Glu Thr Lys Ser Val His
1               5                   10

<210> SEQ ID NO 7
<211> LENGTH: 7
<212> TYPE: PRT
<213> ORGANISM: Homo sapiens

<400> SEQUENCE: 7

Asp Asp Asp Asp Arg Pro Ser
1               5

<210> SEQ ID NO 8
<211> LENGTH: 11
<212> TYPE: PRT
<213> ORGANISM: Homo sapiens

<400> SEQUENCE: 8

Gln Val Trp Asp Asp Asn Asn Asp Glu Trp Val
1               5                   10

<210> SEQ ID NO 9
<211> LENGTH: 121
<212> TYPE: PRT
<213> ORGANISM: Homo sapiens

<400> SEQUENCE: 9

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Lys Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

<210> SEQ ID NO 10
<211> LENGTH: 110
<212> TYPE: PRT
<213> ORGANISM: Homo sapiens

<400> SEQUENCE: 10

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 11
<211> LENGTH: 5
<212> TYPE: PRT
<213> ORGANISM: Homo sapiens

<400> SEQUENCE: 11

Ser Tyr Gly Met His
1               5

<210> SEQ ID NO 12
<211> LENGTH: 17
<212> TYPE: PRT
<213> ORGANISM: Homo sapiens

<400> SEQUENCE: 12

Phe Ile Arg Tyr Asp Gly Ser Asn Lys Tyr Tyr Ala Asp Ser Val Lys
1               5                   10                  15

Gly

<210> SEQ ID NO 13
<211> LENGTH: 12
<212> TYPE: PRT
<213> ORGANISM: Homo sapiens

<400> SEQUENCE: 13

Asp Arg Gly Leu Gly Asp Gly Thr Tyr Phe Asp Tyr
1               5                   10

<210> SEQ ID NO 14
<211> LENGTH: 13
<212> TYPE: PRT
<213> ORGANISM: Homo sapiens

<400> SEQUENCE: 14

Ser Gly Ser Ser Ser Asn Ile Gly Asn Asn Ala Val Asn
1               5                   10

<210> SEQ ID NO 15
<211> LENGTH: 7
<212> TYPE: PRT
<213> ORGANISM: Homo sapiens

<400> SEQUENCE: 15

Tyr Asp Asp Leu Leu Pro Ser
1               5

<210> SEQ ID NO 16
<211> LENGTH: 11
<212> TYPE: PRT
<213> ORGANISM: Homo sapiens

<400> SEQUENCE: 16

Ala Ala Trp Asp Asp Ser Leu Asn Gly Pro Val
1               5                   10

<210> SEQ ID NO 17
<211> LENGTH: 645
<212> TYPE: DNA
<213> ORGANISM: Homo sapiens

<400> SEQUENCE: 17

| cagcctgtgc tgactcagcc atcctcagtg tcagtggccc caggagagac ggccagaatt | 60 |
| ccctgtgggg gagacgacat tgaaactaaa agtgtccact ggtaccagca gaagccaggc | 120 |
| caggcccctg tgctggtcat ctatgatgat gacgaccggc cctcagggat ccctgagcga | 180 |
| ttctttggct ccaactctgg gaatacggcc accctgagta tcagcagggt cgaagccggg | 240 |
| gatgaggccg actattactg tcaggtgtgg gatgacaata atgatgaatg ggtgttcggc | 300 |
| ggaggcaccc agctgaccgt cctcggtcag cccaaggctg ccccctcggt cactctgttc | 360 |
| ccgccctcct ctgaggagct tcaagccaac aaggccacac tggtgtgtct cataagtgac | 420 |
| ttctacccgg gagccgtgac agtggcctgg aaggcagata gcagccccgt caaggcggga | 480 |
| gtggagacca ccacaccctc caaacaaagc aacaacaagt acgcggccag cagctatctg | 540 |
| agcctgacgc ctgagcagtg gaagtccac agaagctaca gctgccaggt cacgcatgaa | 600 |
| gggagcaccg tggagaagac agtggcccct acagaatgtt cataa | 645 |

<210> SEQ ID NO 18
<211> LENGTH: 354
<212> TYPE: DNA
<213> ORGANISM: Homo sapiens

<400> SEQUENCE: 18

| gaggtgcagc tggtggagtc tgggggaggc gtggtccagc ctgggggtc cctgagactc | 60 |
| tcctgtgcag cgtctggatt caccttcagt agctatggca tgcactgggt ccgccaggct | 120 |
| ccaggcaagg ggctggagtg ggtggcattt atacggtatg atggaagtaa taaatactat | 180 |
| gcagactccg tgaagggccg attcaccatc tccagagaca attccaagaa cacgctgtat | 240 |
| ctgcaaatga acagcctgag agctgaggac acggctgtgt attactgtgc gaaagatcgg | 300 |
| tttggttatt atcttgacta ctggggccaa ggaaccctgg tcaccgtctc ctca | 354 |

<210> SEQ ID NO 19
<211> LENGTH: 651
<212> TYPE: DNA
<213> ORGANISM: Homo sapiens

<400> SEQUENCE: 19

| cagtctgccc tgactcagcc tgcctccgtg tctgggtctc ctggacagtc aatcaccatc | 60 |
| tcctgttctg gaagcagctc caacatcgga aataatgctt taactggta ccagcagctc | 120 |

-continued

```
ccaggaaagg ctcccaaact cctcatctat tatgatgacc tactgccctc aggggtctct      180
gaccgattct ctggctccaa gtctggcacc tcagccttcc tggccatcag tgggctccag      240
tctgaggatg aggctgatta ttactgtgca gcatgggatg acagcctgaa tggtccagtg      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgaaggga gcaccgtgga agacacgtg gcccctacag aatgttcata a                651
```

<210> SEQ ID NO 20
<211> LENGTH: 363
<212> TYPE: DNA
<213> ORGANISM: Homo sapiens
<400> SEQUENCE: 20

```
caggtacagc tggtggagtc tgggggaggc ctggtcaagc ctggagggtc cctgagactc       60
tcctgtgcag cgtctggatt caccttcagt agctatggca tgcactgggt ccgccaggct      120
ccaggcaagg ggctggagtg ggtggcattt atacggtatg atggaagtaa taatactat      180 gcagactccg tgaagggccg attcaccatc tccagagaca attccaagaa cacgctgtat      240
ctgcaaatga acagcctgag agctgaggac acggctgtgt attactgtgc gaaagatcga      300 ggtttgggg atggaaccta ctttgactac tggggccaag gaccacggt caccgtctcc      360 tca                                                                   363
```